US009127300B2

(12) United States Patent
Bolea et al.

(10) Patent No.: US 9,127,300 B2
(45) Date of Patent: Sep. 8, 2015

(54) MICROBIAL DETECTION SYSTEM AND METHODS

(75) Inventors: Phillip A. Bolea, Grant, MN (US); Kurt J. Halverson, Lake Elmo, MN (US); Cynthia D. Zook, Hudson, WI (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 13/807,058

(22) PCT Filed: Jun. 27, 2011

(86) PCT No.: PCT/US2011/041939
§ 371 (c)(1),
(2), (4) Date: Feb. 7, 2013

(87) PCT Pub. No.: WO2012/012104
PCT Pub. Date: Jan. 26, 2012

(65) Prior Publication Data
US 2013/0149738 A1 Jun. 13, 2013

Related U.S. Application Data

(60) Provisional application No. 61/360,166, filed on Jun. 30, 2010.

(51) Int. Cl.
*C12Q 1/04* (2006.01)
*C12Q 1/24* (2006.01)

(52) U.S. Cl.
CPC ... *C12Q 1/04* (2013.01); *C12Q 1/24* (2013.01)

(58) Field of Classification Search
CPC .......................................................... C12Q 1/04
USPC .................................................. 435/34, 228.7
See application file for complete search history.

(56) References Cited

U.S. PATENT DOCUMENTS

| 4,565,783 A | 1/1986 | Hansen et al. |
| 5,089,413 A | 2/1992 | Nelson et al. |
| 5,364,766 A * | 11/1994 | Mach et al. ..................... 435/34 |

(Continued)

FOREIGN PATENT DOCUMENTS

| WO | WO 01/83672 | 11/2001 |
| WO | WO 2005/024047 | 3/2005 |
| WO | WO 2009/082667 | 7/2009 |

OTHER PUBLICATIONS

Kikuchi HE et al. (1986). Quantitative Method for Measurement of Aerotolerance of Bacteria and Its Application to Oral Indigenous Anaerobes. Applied and Environmental Microbiology, v52(4), p. 971-973.*

(Continued)

*Primary Examiner* — Cherie M Stanfield
*Assistant Examiner* — Sean C Barron

(57) ABSTRACT

The disclosure provides culture devices and methods for a microorganism in a sample. The devices include a base member, a cover sheet, an adhesive layer coupled to the base member or the cover sheet, and a cold water-soluble gelling agent disposed on the base member; wherein the devices are substantially optically transmissive when the gelling agent is hydrated with a clear liquid. Methods of use include detecting or enumerating microorganisms. The methods further provide for detecting a microorganism by detecting the presence or size of an abiogenic gas bubble in a culture device.

9 Claims, 6 Drawing Sheets

(56) References Cited

U.S. PATENT DOCUMENTS

| | | | |
|---|---|---|---|
| 5,448,652 | A | 9/1995 | Vaidyanathan et al. |
| 5,510,246 | A * | 4/1996 | Morgan .................... 435/39 |
| 5,681,712 | A | 10/1997 | Nelson |
| 5,694,478 | A | 12/1997 | Braier et al. |
| 5,744,322 | A | 4/1998 | Krejcarek et al. |
| 5,879,635 | A | 3/1999 | Nason |
| 6,153,400 | A | 11/2000 | Matsumura et al. |
| 6,243,286 | B1 | 6/2001 | Kumagai et al. |
| 6,243,486 | B1 | 6/2001 | Weiss |
| 2001/0039032 | A1 | 11/2001 | Matsumura et al. |
| 2004/0092001 | A1 | 5/2004 | Bedingham et al. |
| 2004/0101954 | A1 | 5/2004 | Graessle et al. |
| 2004/0102903 | A1 | 5/2004 | Graessle et al. |
| 2011/0143334 | A1 * | 6/2011 | Roscoe et al. .................... 435/5 |

OTHER PUBLICATIONS

Steiglmeier M et al. (2009). Cultivation of Anaerobic and Facultatively Anaerobic Bacteria from Spacecraft-Associated Clean Rooms. Applied and Environmental Microbiology, v75(11), p. 3484-3491.*

Obligate Aerobe. The American Heritage Medical Dictionary. Boston: Houghton Mifflin, 2007.*

Microaerophile. Collins English Dictionary. London: Collins, 2000.*

Aerotolerant. Academic Press Dictionary of Science and Technology. Oxford: Elsevier Science & Technology, 1992.*

Obligate Aerobe. Mosby's Dictionary of Medicine, Nursing, & Health Professions. Philadelphia: Elsevier Health Sciences, 2012.*

Obligate Anaerobe. Mosby's Dictionary of Medicine, Nursing, & Health Professions. Philadelphia: Elsevier Health Sciences, 2012.*

Facultative Anaerobe. Mosby's Dictionary of Medicine, Nursing, & Health Professions. Philadelphia: Elsevier Health Sciences, 2012.*

Microaerophile. Mosby's Dictionary of Medicine, Nursing, & Health Professions. Philadelphia: Elsevier Health Sciences, 2012.*

Kurakov AV et al. (2008). Diversity of Facultatively Anaerobic Microscopic Mycelial Fungi in Soils. Mikrobiologiya, v77(1), p. 103-112.*

Dimitrov LN et al. Polymorphisms in Multiple Genes COntribute to the Spontaneous Mitrochondrial Genome Instability of *Saccharomyces cerevisiae* S228C Strains. Genetics, v183, p. 365-383.*

Waters JR (1992). Detection of Bacterial Growth by Gas Absorption. Journal of Clinical Microbiology, v30(5), p. 1205-1209.*

Gil GC et al. (2000). A biosensor for the detection of gas toxicity using a recombinant bioluminescent bacterium. Biosensors and Bioelectronics, v15, p. 23-30.*

Bibilov et al. (1997). A Signal Transducer for Aerotaxis in *Escherichia coli*. Journal of Bacteriology, v179(12), p. 4075-4079.*

Jung et al. (2000). Catalase Effects on Glucose-Sensitive Hydrogels. Macromolecules, v33, p. 3332-3336.*

Fletcher et al. (1982). Bubble Contact Angle Method for Evaluating Substratum Interfacial Characteristics and Its Relevance to Bacterial Attachment. Applied and Environmental Microbiology, v44(1), p. 184-192.*

Durham et al. (1898). A Simple Method for Demonstrating the Production of Gas by Bacteria. The British Medical Journal, v1(1952), p. 1387.*

US 4,476,226, 10/1984, Hansen et al. (withdrawn)

* cited by examiner

MICROBIAL DETECTION SYSTEM AND METHODS

CROSS REFERENCE TO RELATED APPLICATION

This application claims the benefit of U.S. Provisional Patent Application No. 61/360,166, filed Jun. 30, 2010, which is incorporated herein by reference in its entirety.

BACKGROUND

Traditional culture methods to detect bacteria in a sample typically rely on the contrast between bacterial colonies and the components of the device (e.g., containment vessel, nutrient medium, and gelling agent) to detect the presence and, optionally, the identity of a microorganism in the sample.

There exists a need for simple articles and methods for the detection of bacteria in a sample.

SUMMARY

In view of the current general methods to detect the presence or absence of a microorganism in a sample, the inventive culture devices provide methods for rapid, indicatorless detection of a microorganism in a sample. Advantageously, the inventive devices and methods can be used without indicator reagents, some of which are known to have inhibitory effects on the growth of microorganisms. Additionally, or alternatively, some embodiments of the devices and methods provide for the enumeration of bacteria. In some embodiments, the inventive methods provide for the automated detection and/or enumeration of bacteria.

Thus, in one aspect, the present disclosure provides methods for detecting the presence or absence of a microorganism in a sample. The method can comprise providing a liquid sample and a culture device comprising a base member, a cover layer, and a dry cold water-soluble gelling agent disposed on the base member and/or the cover sheet. The culture device can include an outermost first major surface, an outermost second major surface, and a growth area. The culture device can be configured to form a highly transmissive optical path extending from the outermost first major surface to the outermost second major surface. The method further can comprise hydrating the growth area of the device with the sample, incubating the device for a period of time, illuminating the growth area with a light source, and detecting the presence or absence of a microorganism in the growth area. Detecting the presence or absence of a microorganism can comprise observing an indication of growth. In some embodiments of the methods, the culture device further can comprise an adhesive layer coupled to the base member and/or the cover sheet, wherein the gelling layer is disposed on the adhesive layer(s).

In some embodiments of the methods, illuminating the growth area can comprise illuminating the growth area with the light source positioned facing the first major surface of the culture device. In any of the above embodiments of the method, observing an indication of growth can comprise observing the growth area from an observation position facing the first major surface of the culture device.

In some embodiments of the methods, illuminating the growth area can comprise illuminating the growth area with the light source positioned facing the second major surface of the culture device.

In some embodiments, the methods further can comprise providing a first contrast layer; and prior to detecting the presence or absence of a microorganism, positioning the first contrast layer proximate the second major surface of the culture device. In some embodiments, the methods further can comprise providing a second contrast layer and, prior to detecting the presence or absence of a microorganism, positioning the second contrast layer proximate the second major surface of the culture device.

In any of the above embodiments, detecting the presence or absence of a microorganism can comprise detecting the scattering, absorbance or transmittance of light. In any of the above embodiments, the methods further can comprise adding an indicator reagent, wherein detecting the presence or absence of a microorganism comprises detecting an observable change in the indicator reagent. In any of the above embodiments, detecting the presence or absence of a microorganism can comprise detecting a fluorescent signal.

In another aspect, the present disclosure provides methods for detecting the presence or absence of a microorganism in a sample, comprising providing a sample and a culture device comprising a base member, a cover layer, and a hydrogel comprising a plurality of abiogenic gas bubbles disposed there between; wherein the hydrogel defines a growth area. The culture device can include an outermost first major surface, an outermost second major surface. The methods further comprise inoculating the growth area of the device with the sample at a first point in time, incubating the device for a period of time, illuminating the growth area with a light source, and detecting the presence or absence of a microorganism in the growth area at a second point in time. Detecting the presence or absence of a microorganism can comprise observing an indication of growth. Observing an indication of growth can comprise detecting the diminution or absence of at least one abiogenic gas bubble in the hydrogel at the second point in time.

In some embodiments of the methods, providing the culture device can comprise providing a thin film culture device that includes a dry, cold water-soluble gelling agent, wherein the method further comprises hydrating the gelling agent with an aqueous liquid. In any of the embodiments, the aqueous liquid can comprise the sample.

In some embodiments, the methods further can comprise observing the growth area with regard to the diminished size or absence of the gas bubble at a third point in time and comparing the observations at two points in time. In any of the embodiments, the methods further can comprise providing a first contrast layer and, prior to detecting the presence or absence of a microorganism, positioning the first contrast layer proximate the second major surface of the culture device.

In some embodiments, the methods further can comprise providing a second contrast layer and prior to detecting the presence or absence of a microorganism, positioning the second contrast layer proximate the second major surface of the culture device. In any of the embodiments, detecting the presence or absence of a microorganism can comprise detecting the scattering, absorbance or transmittance of light. In any of the above embodiments, the methods further can comprise adding an indicator reagent, wherein detecting the presence or absence of a microorganism comprises detecting an observable change in the indicator reagent. In any of the embodiments, detecting the presence or absence of a microorganism can comprise enumerating microorganisms. In any of the embodiments, the methods further can comprise providing a first optical filter and, prior to detecting the presence or absence of a microorganism, positioning the first optical filter between the light source and the culture device. In any of the above embodiments, detecting the presence or absence of a microorganism can comprise detecting and differentiating two or more types of microorganisms.

In any of the above embodiments, the methods further can comprise providing an imaging system and obtaining an image of the growth area of the culture device, wherein observing an indication of growth comprises displaying, printing, or analyzing the image of the growth area.

In another aspect, the present disclosure provides devices for detecting microorganisms; comprising a base member, a cover layer, and a cold water soluble gelling agent disposed on the first adhesive layer. The devices are substantially optically transmissible when the gelling agent is hydrated with a clear aqueous liquid. In some embodiments, the device further can comprise a first adhesive layer coupled to one of the base member or the cover layer.

In any of the above embodiments, the devices can further comprise a second adhesive layer coupled to the other of the base member or cover layer. In any of the above embodiments, the devices further can comprise a nutrient medium disposed on the first or second adhesive layer. In any of the above embodiments, the devices further can comprise an optical filter layer or a contrast layer.

In any of the above embodiments, the optical haze of the culture device, after hydration with a clear aqueous liquid, is ≤95% when measured according to ASTM 1003. In any of the above embodiments, the optical clarity of the culture device, after hydration with a clear aqueous liquid, is ≥10% when measured according to ASTM 1003.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a sample suspected of containing "a" microorganism can be interpreted to mean that the sample can include "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

FIG. 4b is an enlarged view of a portion of the culture device of FIG. 4a.

FIG. 5b is an enlarged view of a portion of the culture device of FIG. 5a.

DETAILED DESCRIPTION

Figure 1:
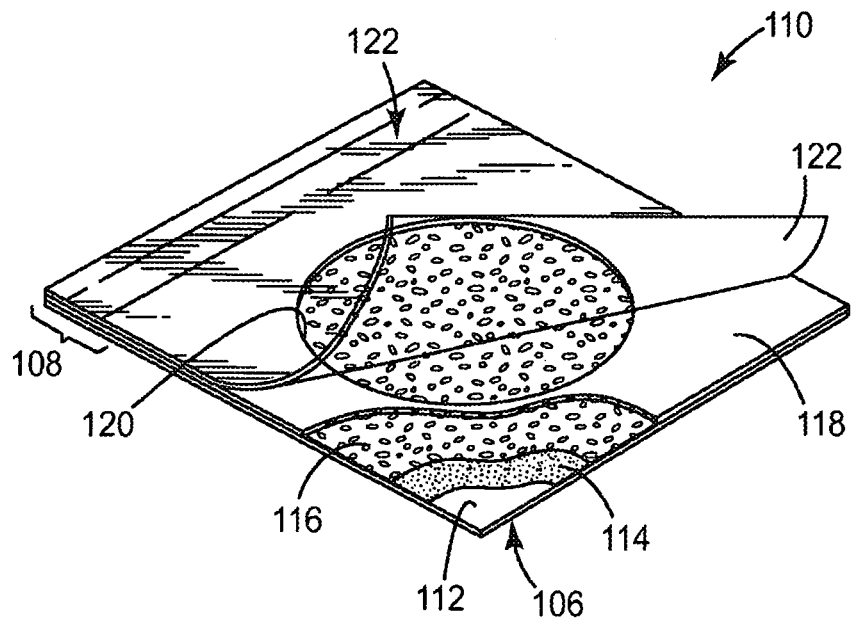
FIG. 1 is a top perspective view, partially in section, of one embodiment of a culture device configured to form a highly-transmissive optical path, according to the present disclosure.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure is generally directed to methods and articles for detecting microorganisms in a sample. In some embodiments, the articles and methods employ substantially optically-transmissive culture devices. The low haze-high clarity devices provide the high contrast needed to distinguish a colony of microorganisms from the materials of the culture device and provide the high spatial resolution to distinguish two microbial colonies that are located very close to one another. In some embodiments, the methods employ the observation of the diminution or disappearance of one or more abiogenic gas bubbles in a culture device as an early indication (e.g., before the appearance of a visible colony) of the presence of a microorganism in a culture device.

The articles and methods are used to detect microorganisms in a sample. Suitable samples can be obtained or derived from a variety of sources. The term "source" is generally used to refer to the food or nonfood desired to be tested for microorganisms. The source can be a solid, a liquid, a semi-solid, a gelatinous material, gas (e.g., air), and combinations thereof. In some embodiments, the source can be provided by a capture element that was used, for example, to collect the source from a surface of interest or from air. In some embodiments, the liquid composition can include the capture element, which can be further broken apart (e.g., during an agitation or dissolution process) to enhance retrieval of the source and any microorganism of interest. The surface of interest can include at least a portion of a variety of surfaces, including, but not limited to, walls (including doors), floors, ceilings, drains, refrigeration systems, ducts (e.g., air ducts), vents, toilet seats, handles, doorknobs, handrails, countertops, tabletops, eating surfaces (e.g., trays, dishes, etc.), working surfaces, equipment surfaces, clothing, etc., and combinations thereof. All or a portion of the source can be used in the method. When a portion of the source is used, this can sometimes be referred to as a "sample" of the source. However, the term "sample" is generally used herein to refer to the portion of volume or mass of material that is obtained from the source and is introduced into a test device for the detection of microorganisms.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

"Sample acquisition device" is used herein in the broadest sense and refers to an implement used to collect a liquid, semisolid, or solid sample material. Nonlimiting examples of sample acquisition devices include swabs, wipes, sponges, scoops, spatulas, tongue depressors, filters, pipettes, pipette tips, and siphon hoses.

"Substantially optically-transmissive", as used herein, refers to an optical path in which the optical haze, as measured by ASTM Method 1003, is less than or equal to about 95% and the optical clarity, as measured by ASTM Method 1003, is greater than or equal to about 10%.

An "abiogenic gas bubble", as used herein, refers to an optically-detectable gas bubble that is produced by means other than biological activity. "Optically-detectable" is used in the broadest sense and includes visual detection by a human as well as detection by machine vision.

Culture Devices:

The present disclosure in certain embodiments includes culture devices for the detection of bacteria. Culture devices of the present invention include, for example, thin film culture plate devices. Thin film culture plate devices are typically more compact than traditional agar petri dishes and typically contain dry, rehydratable culture medium to support the growth of certain microorganisms. Non-limiting examples of thin film culture plate devices include the coated-substrate devices disclosed in U.S. Pat. Nos. 4,565,783; 5,089,413; and 5,681,712; each of which is incorporated herein by reference in its entirety.

FIG. 1 illustrates an embodiment of a culture device 110 in accordance with the present disclosure. The culture device 110 comprises a base 112 and a cover sheet 122. The culture device 110 includes an outermost first major surface 104 and an outermost second major surface 106. The culture device 110, when inoculated with a liquid sample, is configured to form a highly transmissive optical path extending from the first major surface to the second major surface.

Optionally, the base 112 and the cover sheet 122 can be coupled together (e.g., in a hinge region 108 using any suitable coupling means (not shown) known in the art, such as a staple, an adhesive, an adhesive tape, double-sided adhesive tape or the like). At least a portion of either the base 112 and/or the cover sheet 122 comprises a coating. As shown in FIG. 1, the base 112 comprises a coating that includes an optional adhesive layer 114 and a gelling layer 116. Optionally, the culture device may further include a spacer 118. The spacer 118 includes an aperture 120, which defines the boundary of a growth area 126.

In the illustrated embodiment, the growth area 126 is circular. The walls of aperture 120 provide a well of predetermined size and shape (e.g., circle, oval, square, rectangle, etc.) to confine a liquid sample (not shown) deposited therein. The aperture 120 generally delineates the boundary of a growth area 126 of the culture device 110. Spacer 118 should be thick enough to form a well of the desired volume, e.g., 1, 2 or 3 milliliters. Closed cell polyethylene or polystyrene foams are preferred materials for spacer 118, but any material which is hydrophobic (non-wetting), inert to microorganisms, and capable of withstanding sterilization may be used. In some embodiments (not shown), the spacer 118 can comprise a plurality of apertures 20 (e.g., 2, 3, 4, 5, 6, 7, 8, 9, 10, 12, 15, or 20 apertures), each of which can be inoculated with a distinct liquid sample.

The thickness of spacer 118 should be sufficient to enclose the liquid volume added to the culture device when the device is inoculated. Depending upon the thickness of the membrane, when used, the spacer 118 can be at least about 0.5 mm thick, about 1 mm thick, about 1.5 mm thick and about 2 mm thick.

The base 112 and cover layer 122 are fabricated using an optically-transmissive material. Preferably, the base 112 and cover layer 122 are transparent. Suitable materials for the base 112 and cover layer 122 include, for example, polyethylene, polypropylene, polycarbonate or polyester films, for example. The major surfaces of the base 112 and cover layer 122 should be substantially flat and smooth and should not include surface features (e.g., pits, bumps, ridges, embossed patterns) that reduce optical clarity by scattering light, for example.

Optional adhesive layer 114 can comprise a variety of adhesives (e.g., pressure-sensitive adhesives) known in the art. Examples of suitable adhesives include copolymer silicone adhesives (e.g., the silicone adhesives described in U.S. Pat. No. 6,703,120, for example, which is incorporated herein by reference in its entirety) and acrylate adhesives (e.g., the acrylate adhesives described in U.S. Pat. No. 4,565,783, for example, which is incorporated herein by reference in its entirety). The adhesive layer 114 can be applied to the base member 112 and/or the cover sheet 122 using processes known in the art (e.g., knife-coating, extrusion, laminative transfer from a release liner, etc.). When applying the adhesive layer 114 to the base member 112 and/or cover sheet 122, care must be taken to minimize the introduction of light-scattering features into (e.g., bubbles) or onto (e.g., craters, pits, bumps, ridges, valleys, channels, or the like) because such features can reduce the optical clarity of the culture device 110.

Thus, the base member 112, cover sheet 122, and adhesive layer 114 are selected from materials with high optical clarity and are processed in a manner to provide a high degree of optical clarity in the culture device 110. Optical clarity can be measured by methods that are known in the art. Optical transmittance is related to optical clarity and can be measured can be measured using ASTM Method 1003, for example. Percent clarity is related to optical clarity and can be measured can be measured using ASTM Method 1003, for example. Percent haze is related to optical clarity and can be measured can be measured using ASTM Method 1003, for example.

The gelling agent used in the gelling layer 116 comprises a cold water-soluble gelling agent. Suitable cold water-soluble gelling agents include, for example, guar gum, xanthan gum, locust bean gum, hydroxyethylcellulose, carboxymethylcellulose, polyacrylamide, algin, and a combination of any two or more of the foregoing. After a liquid sample is deposited between the base member 112 and the cover sheet 122, the liquid causes the gelling agent to swell, thereby forming a hydrogel containing the liquid sample.

In any of the embodiments, the gelling layer 116 may further comprise a nutrient to facilitate the growth of a microorganism. In any of the embodiments, the gelling layer 116 may further comprise a selective agent to select for the growth of a specific microorganism or group of microorganisms. In some embodiments, the gelling agent, optional nutrients and optional selective agents can be powder-coated onto the adhesive layer 114, as described in U.S. Pat. No. 4,565,783, for example.

In another embodiment of the invention, powder 116 may comprise a coating that includes a mixture of a gelling agent and a nutrient, a selective agent, and/or an indicator reagent which has been dissolved or suspended in a solution, coated and dried onto substrate 112. In this embodiment, the coating is substantially water-free (i.e., the coating has a water content no greater than about the water content of the dehydrated coating once it has been permitted to equilibrate with the ambient environment).

The specific nutrients and/or selective agents used in the culture device will be apparent to those skilled in the art in view of the present specification and may be optimized for the particular bacteria to be grown and/or to be selectively detected or inhibited. For example, certain selective agents (e.g., antibiotics such as vancomycin) may be added to the composition to select for corresponding antibiotic-resistant microorganisms. Additionally, the concentration of the selective agent can be adjusted to select for a certain level of resistance, which is well known to a person of ordinary skill in the art.

Culture devices of the present disclosure may optionally include an indicator reagent. The indicator reagent may be incorporated into the gelling layer, as described above, and/or incorporated into the adhesive layer, as described in U.S. Pat. No. 4,565,783, for example.

An exemplary useful class of indicator reagents include dyes that are metabolized by, or otherwise react with, growing microorganisms, and in so doing cause the microbial colonies to be colored or fluoresce for ease of detection and/or quantitation by a technician or by an automated reader. Nonlimiting examples of such dyes include triphenyltetrazolium chloride, p-tolyltetrazolium red, tetrazolium violet, veratryl tetrazolium blue, and 5-bromo-4-chloro-3-indolyl phosphate disodium salt. However, it will be appreciated that other suitable dyes can be used depending on the particular organism(s) to be identified.

A buffering reagent, such as sodium carbonate, can be employed to provide a medium exhibiting a neutral pH and "Cab-O-Sil M-5" can be employed as a processing aid for powder-coated mixtures, as described in U.S. Pat. No. 4,565,783, which is incorporated herein by reference in its entirety. Of course, the particular coating mixture (e.g., nutrients, indicator reagents, and/or gelling agents) used for powder 116 may be adjusted depending upon the type of microorganisms to be grown.

It is contemplated that articles of the present disclosure can include differential indicator reagents. As used herein, "differential indicator reagent" refers to a reagent added to the medium that will indicate the presence of certain microorganisms and not other microorganisms. Nonlimiting examples of differential indicator reagents include dyes (e.g., stains, pH indicators, redox indicators), enzyme substrates (e.g., chromogenic or fluorogenic substrates for phosphatases, glycosidases, peptidases, nucleases, lipases, and the like), and specific nutrients (e.g., fermentable carbohydrates, amino acids) which, when metabolized by certain microorganisms, produce a detectable reaction (e.g., a pH indicator changing color within or adjacent a colony).

In some embodiments, one or more differential indicator reagents can be added to the thin film culture device in the water-based composition that is coated onto the substrate. In some embodiments, one or more differential indicator reagents can be added to the liquid sample that is added to the culture device.

In the embodiments (not shown) wherein the culture device does not include a spacer 118 to confine the sample during inoculation, a template, e.g., a weighted ring (not shown), may be applied temporarily to the outside of cover sheet, after closing, to confine the sample to a specific region while the cold-water-soluble powder forms a gel. The portion of the culture device inoculated with a sample generally delineates the growth area 126 of the device.

In one embodiment, a thin film culture plate device can be made by producing a liquid coating mixture, coating the liquid coating mixture onto a substrate, drying the coated substrate and, optionally, attaching a cover sheet according to processes described in U.S. Pat. No. 4,565,783, for example.

In use, a predetermined amount of inoculum, typically about one milliliter of a liquid inoculum is added to the device by pulling back cover sheet 122 and depositing the inoculum onto the gelling layer 116. The inoculum may optionally comprise a nutrient, a selective agent, an indicator reagent or a combination of any two or more of the foregoing. Cover sheet 122 is then replaced over the base member 112 and the inoculum is evenly spread inside the opening of the spacer 118, if present. A convenient tool to do this is a generally flat, weighted article that is shaped and dimensioned to conform to the growth area 126 of the culture device 110. The inoculated device 110 is then incubated for a predetermined time after which the number of bacterial colonies growing on the substrate may be observed through the cover sheet 122 and counted.

A preferred coating mixture, when hydrated with a predetermined volume of sample, can comprise the ingredients of the culture medium at the concentrations shown in Table 1. In some embodiments, the coating mixture for the culture device can comprise some of the ingredients shown in Table 1 and a liquid (e.g., a diluent) containing the sample can comprise some or all of the remaining ingredients shown in Table 1. Thus, the addition of the ingredients in the culture device and the ingredients in the diluent can result in the culture medium shown in Table 1.

TABLE 1

Composition of an exemplary culture medium.

| Ingredient | Amount (milligrams/mL) |
| --- | --- |
| Tryptone | 3.3 |
| Proteose Peptone No. 3 | 10 |
| Bacto Peptamin | 10 |
| Yeast Extract | 7.3 |
| Dextrose | 20.6 |
| Sodium Pyruvate | 6.6 |
| Meat Extract | 15 |
| $K_2HPO_4$ | 3.3 |
| $KH_2PO_4$ | 0.4 |
| Guar gum | 25-50 |

Optionally, the culture medium can comprise a buffer. Suitable buffers include phosphate buffers. In some embodiments, the carbonate buffer is a sodium carbonate buffer. In some embodiments, the phosphate buffer is a potassium phosphate buffer. In some embodiments, the culture medium can comprise more than one buffering agent (e.g., potassium phosphate and sodium acetate). The phosphate buffer can be about 22 mM.

The concentration of each component in the culture medium is selected to provide a concentration suitable for growth and/or detection of the target microorganisms after the culture device has been inoculated. Suitable concentrations of nutrients and selective agents for growing specific microorganisms in culture media are known in the art.

The selection of target microorganisms may include inhibiting the growth of non-non-target microorganisms, promoting the growth of non-target microorganisms, or both. Promoting the growth of target microorganisms may be provided by the at least one first selective agent either directly (e.g., a nutrient that can be used by target microorganisms and not by other microorganisms), indirectly (e.g., by reducing competition for nutrients by inhibiting non-target microorganisms), or both directly and indirectly. Any element, radical, ion, or compound that selects for the growth of target microorganisms may be suitable for use as a selective agent.

A dry culture medium according to the present invention may be applied to one or more surfaces of a thin film culture device in the following manner. The components of the culture medium may be dissolved in a solvent (e.g., water). The resulting solution may then be coated onto one or more surfaces of the device. The coating is then allowed to dry, leaving dried culture medium on the surfaces of the device that had been coated with the culture medium solution. The coating may be dried in any suitable manner including, but not limited to, air drying and heating.

The quantity of each component of the dry culture medium is at least partially determined by at least two factors: (1) the concentration of that component in the culture medium solution, and (2) the amount of the solution coated onto a given surface area of the culture device (the coating weight). Suitable coating weights may range from about 0.45 mg/cm$^2$ to about 2.5 mg/cm$^2$. In some embodiments, the culture medium nutrients may be coated separately from the indicator reagents. In such embodiments, the coating weight for the culture medium nutrients may range from about 1.6 mg/cm$^2$ to about 2.5 mg/cm$^2$. In one embodiment, the coating weight of the nutrient coating is about 2.1 mg/cm$^2$. The coating weight for the indicator coating may range from about 0.45 mg/cm$^2$ to about 0.84 mg/cm$^2$. In one embodiment, the coating weight of the indicator coating is about 0.62 mg/cm$^2$.

Figure 2:
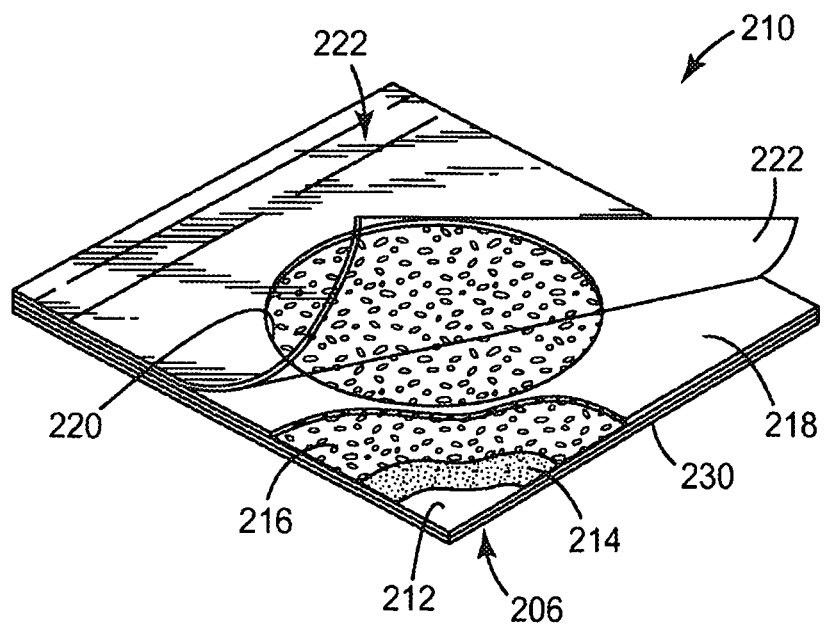
FIG. 2 is a top view, partially in section, of one embodiment of a culture device with a contrast layer according to the present disclosure.

Turning back to the drawings, FIG. 2 shows another embodiment of a culture device 210 according to the present disclosure. The device 210 comprises a base member 212, cover sheet 222, adhesive layer 214, optional spacer 218, and gelling layer 216, as described for the culture device 110 of FIG. 1. In addition, the culture device 210 further comprises a contrast layer 230 positioned proximate the second major surface of the culture device 210

The contrast layer 230 can be fabricated from any suitable material to reflect, absorb, or diffuse (e.g., scatter) selected wavelengths of light. Suitable materials include, for example, cellulosic material, metal, glass, organic polymers or inorganic polymers. The materials may be blended with compounds (e.g., pigments, dyes, particles) that absorb, reflect, or diffuse selected wavelengths of light. The contrasting layer 230 may comprise a uniform surface facing the culture device 210.

In some embodiments, the contrast layer 230 may comprise a reflective layer, such as metal, metal foil, a metalized polymeric film, or a mirror, for example. In some embodiments, the contrast layer 230 may comprise a specularly-reflective layer, such as the specularly-reflective film. An example of a suitable specularly-reflective layer is a Vikuiti Enhanced Specular Reflective (ESR) Film (part number 98044027500) obtained from 3M Company in St. Paul, Minn.

In some embodiments, the contrast layer 230 may be coupled (e.g., adhesively coupled) to the culture device 210. In an alternative embodiment, the contrast layer 230 may be a composition that is coated onto the base member 212 of the culture device 210.

Samples

Suitable test samples can be derived from any source. Samples of interest may include liquids (e.g., beverages, process streams, water), solids (e.g., food ingredients, plants, meat, air, surfaces (e.g., floors, walls, instruments, food-processing equipment), and the like. Samples can also include cultured cells (e.g., bacterial cultures, enrichment broths).

Various sampling techniques for the detection of microbes on surfaces are known. Such sampling techniques are suitable for the methods of the present invention as well. For example, it is common to obtain a sample from wiping the surface of food processing equipment or from wiping the nares of a patient. A particularly preferred sampling technique includes contacting (e.g., swabbing, wiping) the surface with a sterile swab, sponge, or sampling device.

A wide variety of swabs or other sample collection devices are commercially available, for example, from 3M Company, St. Paul Minn., under the trade designation 3M™ Quick Swab, from Puritan Medical Products Co. LLC, Guilford, Me., under the trade designation PURE-WRAPS or from Copan Diagnostics, Inc. Corona, Calif., under the trade designation ESWAB, or from microRheologics, S.r.l., Brescia, I T, under the trade designation FLOCKEDSWAB. A sample collection means such as that disclosed, for example, in U.S. Pat. No. 5,879,635 (Nason) can also be used if desired. Swabs can be of a variety of materials including cotton, rayon, calcium alginate, Dacron, polyester, nylon, polyurethane, and the like.

The sample collection device (e.g., swab) can then be cultured directly, analyzed directly, or extracted (e.g., by washing, elution by vortexing) with an appropriate solution. Such extraction (i.e., elution) solutions typically include water and can optionally include a buffer and at least one surfactant. An example of an elution buffer includes, for example, phosphate buffered saline (PBS), which can be used in combination, for example, with TWEEN 20 or PLURONIC L64. The test sample (e.g., liquid) may be subjected to treatment prior to further analysis. This includes concentration, precipitation, filtration, centrifugation, dialysis, dilution, inactivation of natural components, addition of reagents, chemical treatment, etc.

Methods for Detecting a Microorganism in a Sample

The present disclosure provides methods for detecting bacteria in a sample. In some embodiments, the method comprises providing a liquid sample and a culture device comprising a base member, a cover layer, and adhesive layer coupled to the base member and or cover sheet, and a dry cold water-soluble gelling agent disposed on the adhesive layer, the device configured to form a highly transmissive optical path.

In any embodiment, the method further can comprise hydrating the growth area of the device with the sample. The sample originally may be a liquid sample (e.g., milk, process water) and/or or a solid sample (e.g., food, food ingredients, environmental residues). The liquid or solid sample may be dissolved or suspended in a liquid medium (e.g., water, a buffer). The culture device is opened (e.g., by lifting the cover sheet to separate it from at least a portion of the base member) and the liquid containing the sample is transferred (e.g., pipetted or poured) into the growth area between the base member and the cover sheet, thereby bringing the liquid sample into contact with the gelling agent. After contact with the liquid sample, the gelling agent hydrates to for a hydrogel.

In any embodiment, the method further can comprise incubating the device for a period of time. The period of time may be a predetermined period of time. In some embodiments, the culture device can be incubated for at least about 8 hours, at least about 12 hours, at least about 18 hours, at least about 24 hours, at least about 48 hours, or at least about 72 hours. In some embodiments, the culture device can be incubated not more than about 24 hours, not more than about 48 hours, or not more than about 72 hours. The incubation temperature is selected according to the microorganism to be detected. A person of ordinary skill in the art will select an appropriate incubation temperature (e.g., about 25° C., about 30° C., about 35° C., about 37°) for the microorganism to be detected.

In any embodiment, the method further comprises detecting the presence or absence of a microorganism in the growth area. Detecting the presence or absence of a microorganism comprises illuminating the growth area with a light source. In some embodiments, the light source (e.g., a white light) may provide a relatively broad-spectrum of wavelengths. In some embodiments, the light source may provide a relatively narrow band of selected wavelengths (e.g., an optically-filtered white light or an ultraviolet light).

In any embodiment, the method further comprises observing an indication of growth. In some embodiments, the indication of growth may be observed by a person visually. In some embodiments, the indication of growth may be observed using an imaging device. In some embodiments, the imaging device may be display or print an image of the growth area such that a person can visually observe and analyze the displayed or printed image. In some embodiments, the imaging device may analyze an image of the growth area using a processor and the results of the analysis can be stored in electronic memory, displayed, and/or printed.

Observing an indication of growth includes observing an object in the highly-transmissive optical path of the culture device. For example, the object may be a microbial colony that reflects, absorbs, or refracts light from the light source. The colony may be observed as a bright spot, a dark spot, or a colored spot that contrasts with the hydrogel proximate the colony. Advantageously, selecting the components of the optical device (e.g., the base member, adhesive layer, and cover sheet) for high optical transmissivity, provides enhanced contrast in order to detect microbial colonies at a relatively early stage of growth.

Figure 6:
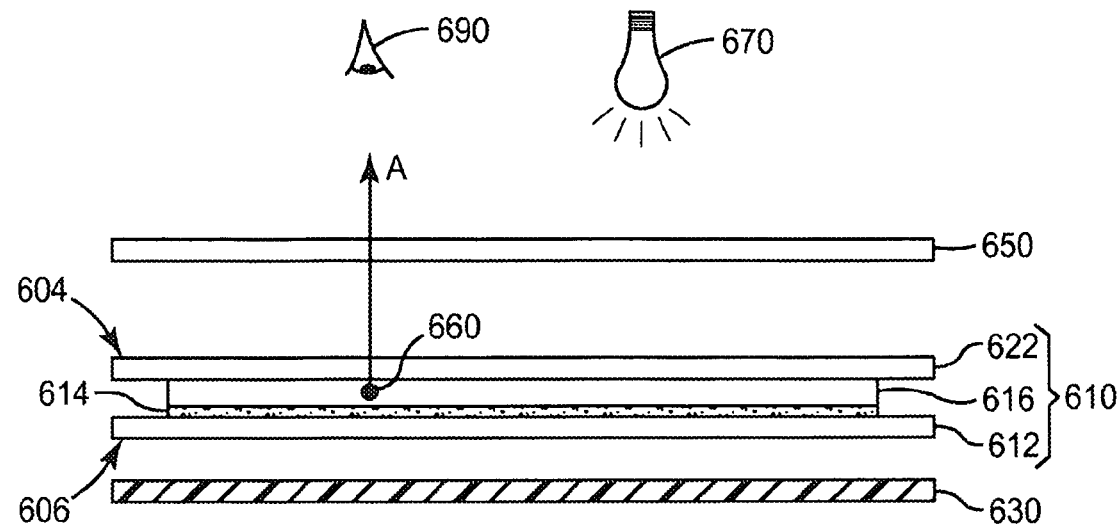
FIG. 6 is a side view of one embodiment of the detection of a microbial colony in a culture device configured to form a highly-transmissive optical path, according to the present disclosure.

FIG. 6 shows one embodiment of detecting the presence or absence of a microorganism in a sample according to the present disclosure. The embodiment includes providing a culture device 610 (shown in side view) configured to form a highly-transmissible optical path extending from an outermost first major surface 604 to an outermost second major surface 606. The culture device 610 includes a base member 612, an optional adhesive layer 614 coupled to the base member 612, a cover sheet 622, and a hydrogel 617 (e.g., a hydrated gelling layer) disposed between the adhesive layer 614 and the cover sheet 622. In the illustrated embodiment, the hydrogel 617 is hydrated with a liquid sample.

The culture device 610 is illuminated by photons from a light source 670. The photons can generally pass through the optically-transmissive culture device 610. A microorganism present in the original sample can form a microbial colony 660 in the hydrogel 617 of the culture device 610. Photons from the light source 670 can strike the microbial colony 660 where they can be reflected (shown as photon "A", which is reflected toward observer 690) or absorbed, causing an observable bright spot, dark spot or colored spot that contrasts with the brightness and/or color of the components of the culture device 610 (e.g., the cover layer, the gelling layer, the adhesive layer, and/or the base member). In the illustrated embodiment, the light source is positioned facing the first major surface 604 of the culture device 610. In the illustrated embodiment, observing an indication of growth comprises observing the growth area from an observation position (i.e., observer 690) facing the first major surface of the culture device.

In some embodiments of the method, observing an indication of microbial growth further comprises providing an optical filter 650 and positioning the optical filter 650 between the light source 670 and the culture device 610. In these embodiments, the culture device 610 can be illuminated with selected wavelengths of light (e.g., red wavelengths, blue wavelengths, ultraviolet wavelengths). This configuration can be particularly advantageous when the color of a microbial colony 660 is only slightly different from the color of one or more components of the culture device 610.

In some embodiments of the method (not shown), observing an indication of microbial growth can comprise observing the culture device with the observer facing the second major surface of the culture device. In these embodiments (i.e., where the light source faces the first major surface of the culture device, and the observer faces the second major surface of the culture device, detecting the presence or absence of a microorganism can comprise detecting the scattering, absorbance or transmittance of light by a colony of microorganisms and/or by an indicator reagent.

In some embodiments of the method, observing an indication of microbial growth further comprises providing a contrast layer 630 and, prior to observing the culture device 610, positioning the contrast layer 630 proximate the second major surface 606 of the culture device 610. In these embodiments, the contrast layer 630 substantially reflects or absorbs the photons from the light source 670 and thereby increasing the contrast between the microbial colony 660 and one or more of the components of the culture device 610. Suitable contrast layers 630 of these embodiments include any of the contrast layers described herein. The contrast layer 630 can be positioned such that it overlaps all or any portion of the growth area (not shown) of the culture device 610.

In some embodiments of the method (not shown), observing an indication of microbial growth further comprises, prior to observing the culture device, positioning a second contrast layer proximate the second major surface of the culture device, illuminating the culture device from a light source positioned facing the first major surface of the culture device, and observing an indication of microbial growth. These embodiments may be particularly advantageous in detecting two distinct microorganisms (e.g., distinct species; distinct genera; and distinct groups such as coliforms, for example). Thus, these embodiments may provide for the detection and differentiation of microorganisms. In some implementations, these embodiments may provide for the confirmation of a particular species, genus, or group of microorganisms. For example, the first contrast layer may provide the observation of a presumptive indication (e.g., $CO_2$ production from the metabolism of lactose by a coliform microorganism) of the presence of a particular microorganism and the second contrast layer may provide the observation of a confirmatory indication (e.g., hydrolysis of a chromogenic enzyme substrate for the β-galactosidase enzyme found in coliform microorganisms) of the presence of the microorganism. In these embodiments, observing an indication of growth comprises observing the growth area from an observation position facing the first major surface of the culture device.

In some embodiments of the method, observing an indication of microbial growth further comprises detecting an observable change in an indicator reagent (e.g., a pH indicator reagent or a chromogenic or fluorogenic enzyme substrate). In these embodiments, the indicator reagent may change to a derivative (e.g., a protonated indicator reagent, a hydrolysed indicator reagent) wherein the change in the indicator reagent (e.g., a color change or fluorescence change) provides an observable bright spot, dark spot, or color change in and/or adjacent the microbial colony 660. Suitable indicator reagents include, for example fluorescent or fluorogenic molecules and bioluminescent compounds.

Figure 7:
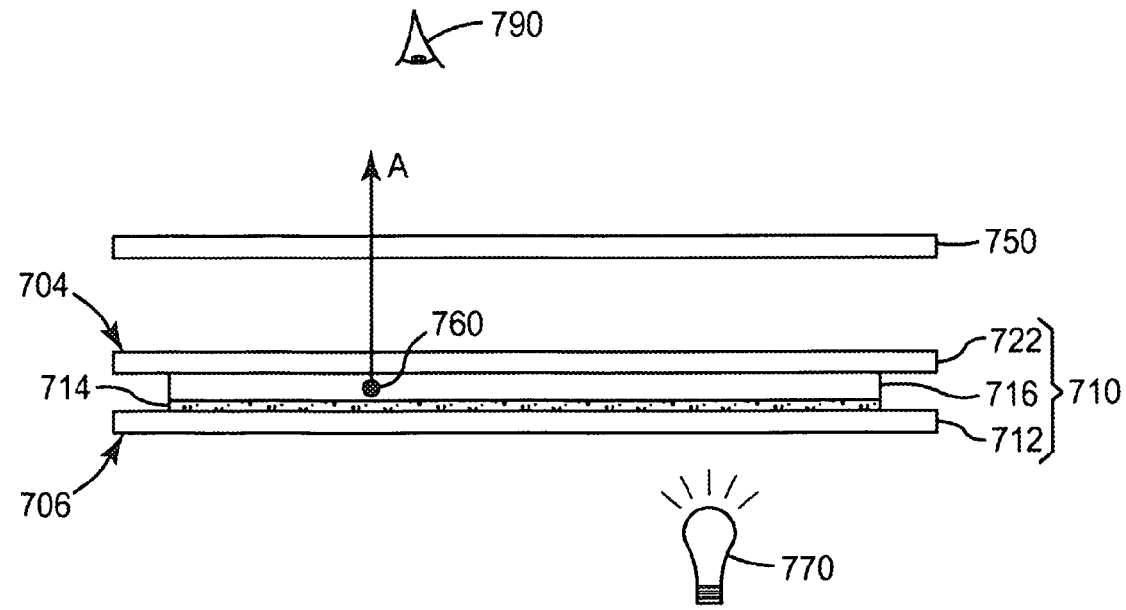
FIG. 7 is a side view of another embodiment of the detection of a microbial colony in a culture device configured to form a highly-transmissive optical path, according to the present disclosure.

In other embodiments of the method, observing an indication of microbial growth comprises positioning an observer facing the first major surface of a culture device and positioning a light source facing the second major surface of the culture device, as shown in FIG. 7.

The illustrated embodiment of FIG. 7 includes providing a culture device 710 (shown in side view) configured to form a highly-transmissible optical path extending from an outermost first major surface 704 to an outermost second major surface 706. The culture device 710 includes a base member 712, an optional adhesive layer 714 coupled to the base member 712, a cover sheet 722, and a gelling layer 716 disposed between the adhesive layer 714 and the cover sheet 722. In the illustrated embodiment, the gelling layer 716 is hydrated with a liquid sample.

The culture device 10 is illuminated by photons from a light source 770. The photons can generally pass through the optically-transmissive culture device 710. A microorganism present in the original sample can form a microbial colony 760 in the gelling layer 716 of the culture device 710. Photons from the light source 770 can strike the microbial colony 760 where they can be reflected (shown as photon "A", which is reflected toward observer 790), transmitted, or absorbed, causing an observable bright spot, dark spot or colored spot that contrasts with the brightness and/or color of the components of the culture device 710 (e.g., the cover layer, the gelling layer, the adhesive layer, and/or the base member). In the illustrated embodiment, the light source 770 is positioned facing the second major surface 706 of the culture device 710. In the illustrated embodiment, observing an indication of growth comprises observing the growth area from an observation position (i.e., observer 790) facing the first major surface 704 of the culture device 710.

In some embodiments of the method, observing an indication of microbial growth further comprises providing an optical filter (not shown) and positioning the optical filter between the light source 770 and the culture device 710. In these embodiments, the culture device 710 can be illuminated with selected wavelengths of light (e.g., red wavelengths, blue wavelengths, ultraviolet wavelengths). This configuration can be particularly advantageous when the color of a microbial colony 760 is only slightly different from the color of one or more components of the culture device 710.

In these embodiments (i.e., where the light source faces the second major surface of the culture device, and the observer faces the second major surface of the culture device, detecting the presence or absence of a microorganism can comprise detecting the scattering, absorbance or transmittance of light by a colony of microorganisms and/or by an indicator reagent.

Detecting the Presence or Absence of a Microorganism by Observing an Abiogenic Gas Bubble:

In another aspect, the present disclosure provides methods for detecting the presence or absence of a microorganism by observing the presence or size of an abiogenic gas bubble. The methods comprise providing a sample and a culture device comprising a base member, a cover layer, and a hydrogel disposed there between. The hydrogel includes a plurality of abiogenic gas bubbles distributed therein. The hydrogel defines a growth area in the culture device. The methods further comprise inoculating the growth area of the device with the sample, incubating the device for a period of time, illuminating the culture device with a light source, and detecting the presence or absence of a microorganism in the culture device by detecting the diminution or absence of at least one abiogenic gas bubble in the culture device at a first point in time. These methods advantageously can be used to detect the presence of a microbial colony before the colony can be detected by other means (e.g., by visual detection of the colony, by detecting a change in the optical properties of an indicator (e.g., a chromogenic enzyme substrate a fluorogenic enzyme substrate, a Ph indicator, a redox indicator) wherein the change is associated with the presence of the microbial colony).

In some embodiments, the growth area of the culture device comprises at least one nutrient to support the growth of a microorganism. The growth area of the culture device may further comprise at least one selective agent to select for the growth of a particular microorganism or group of microorganisms (e.g., antibiotic-resistant microorganisms). The nutrients and/or selective agents to favor the growth of a particular organism or group of organisms (e.g., aerobic bacteria) are known to a person of ordinary skill in the art. The nutrient or selective agent should be selected such that it does not substantially interfere with the formation and/or observation of abiogenic gas bubbles in the hydrogel.

In some embodiments, the hydrogel is in uniform contact with the base member and cover layer of the culture device throughout the growth area of the device (i.e., the hydrogel is "sandwiched" between the base member and the cover layer). In some embodiments, the culture device can be a thin film culture device such as the devices disclosed in U.S. Pat. No. 4,565,783. In some embodiments, the culture device can be a highly optically-transmissive culture device according to the present disclosure.

The abiogenic gas bubbles can be formed in the device spontaneously when the device is hydrated with an aqueous liquid or inoculated with a liquid sample (e.g., an aqueous liquid sample). Without being bound by theory, abiogenic gas bubbles can be formed when a dry, cold-water soluble gelling agent is hydrated with an aqueous sample, causing air bubbles to become entrapped in the hydrogel as the gelling agent swells. It may take about several minutes to about several hours for the abiogenic gas bubbles to become observable in the culture device after the device is hydrated or inoculated. The abiogenic gas bubbles may be regularly distributed or randomly distributed throughout the growth area of the culture device. Preferably, the abiogenic gas bubbles are uniformly distributed throughout the growth area of the culture device. In certain preferred embodiments, the abiogenic gas bubbles are approximately uniform in size. In some embodiments, the abiogenic gas bubbles are less than about 1 mm in diameter. In certain preferred embodiments, the abiogenic gas bubbles are about 0.5 mm to about 1.0 mm in diameter. In some embodiments, the abiogenic gas bubbles are less than about 0.5 mm in diameter. In general, smaller, uniformly distributed abiogenic gas bubbles can permit greater sensitivity and resolution of the detection of separate colonies of microorganisms in the culture device.

The number and spatial distribution of abiogenic gas bubbles can facilitate the detection of a microorganism in the culture device. Preferably, there are about 50-100 abiogenic gas bubbles per square centimeter of hydrogel. More preferably, there are about 100 to about 500 abiogenic gas bubbles per square centimeter of hydrogel. In some embodiments, there are about 200 abiogenic gas bubbles per square centimeter.

The growth area of the culture device is inoculated with a sample. In some embodiments, the hydrogel is formed by hydrating a gelling agent (e.g., a cold water-soluble gelling agent) with an aqueous liquid (e.g., sterile water, sterile buffer). In these embodiments, the culture device can be opened (e.g., by lifting the cover layer) to expose at least a portion of the hydrogel and the hydrogel can be contacted with a sample. For example, a sample collection device (e.g., a swab) can be contacted with the hydrogel to transfer a solid or liquid sample to the culture device. In alternative embodiments, a liquid sample can be pipetted onto the hydrogel. In further alternative embodiments, the hydrogel can be brought into contact with a surface (e.g., equipment, a floor, a wall) to inoculate the hydrogel with material that was present on the surface (e.g., dirt, dust, residues). After inoculation of the hydrogel, the culture device is closed.

In the embodiments where the culture device comprises a dry, rehydratable cold water-soluble gelling agent, the hydrogel can be formed by contacting the dry gelling agent with a predetermined volume (e.g., about 1 mL, about 5 mL) of aqueous liquid comprising the sample.

In some embodiments, the culture device can comprise a nutrient to support the growth of a microorganism, as described above. Alternatively or additionally, a nutrient to support the growth of a microorganism is provided in the liquid sample (e.g., the liquid sample is mixed with a nutrient prior to inoculating the device with the liquid sample). After inoculation, the culture device can be incubated for a period of time, as described herein.

After inoculation, and before substantial microbial growth has occurred in the culture device (e.g., less than the time it takes about 1-2 cell divisions to occur), the culture device may be observed or imaged to compare with the same culture device after substantial microbial growth has occurred. Alternatively, a similar culture device can be inoculated with a sterile liquid as a control.

After incubation, the culture device can be observed for an indication of the presence or absence of a microorganism. The presence of a microorganism can be indicated by a discontinuity of a plurality of abiogenic gas bubbles in the culture device at a first point in time. That is, the culture device can be observed for the presence of a plurality of abiogenic gas bubbles distributed in the growth area. A discontinuity can be observed when, within a region of the growth area, one or more of the abiogenic gas bubbles are substantially smaller than the typical abiogenic gas bubbles in the growth area and/or there is an area in which one or more abiogenic gas bubbles are absent. Without being bound by theory, the abiogenic gas bubbles may diminish in size or disappear by the metabolism of gasses (oxygen, carbon dioxide, and/or nitrogen) by a microorganism or by the microbial production of surfactants that disperse one or more abiogenic gas bubbles. In some embodiments, the presence of a discontinuity of abiogenic gas bubbles in the culture device can be more apparent when the culture device is observed (or imaged) at two or more time points (e.g., before substantial microbial growth has occurred and after microbial growth has occurred) and the observations at each point in time are compared.

Figure 3:
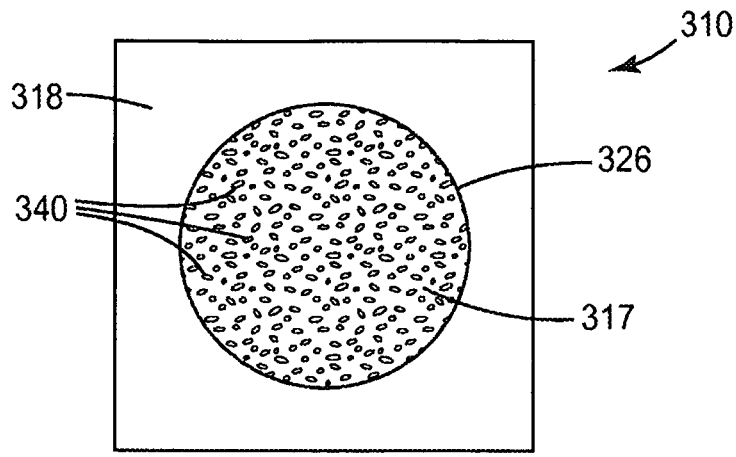
FIG. 3 is a top view of one embodiment of a culture device comprising a hydrogel with a plurality of abiogenic gas bubbles distributed therein at a first point in time, according to the present disclosure.

Turning to the drawings, FIG. 3. shows a top view of one embodiment of a culture device at a first point in time. The culture device comprises abiogenic bubbles. The culture device 310 illustrated in FIG. 3 represents a culture device 310 after which the abiogenic gas bubbles 340 have formed in the device but before substantial microbial growth has occurred (e.g., within about 1 to about 15 minutes after inoculation. The culture device 310 includes a circular growth area 326 bounded by a spacer 318 containing abiogenic gas bubbles 340 in a hydrogel 317. The gas bubbles 340 are randomly distributed throughout the growth area 326.

Figure 4A:
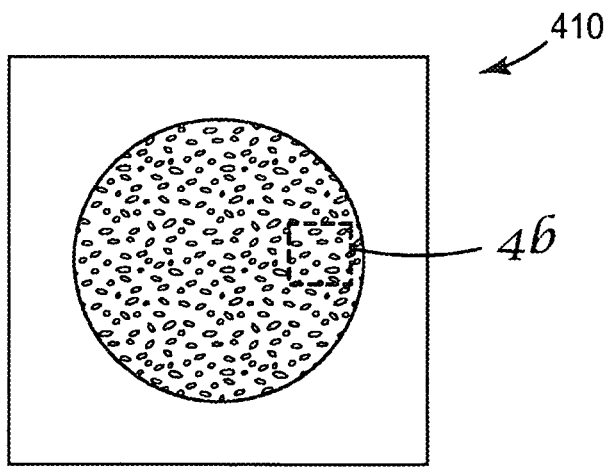
FIG. 4a is a top view of the culture device of FIG. 3 at a second point in time.
Figure 4B:
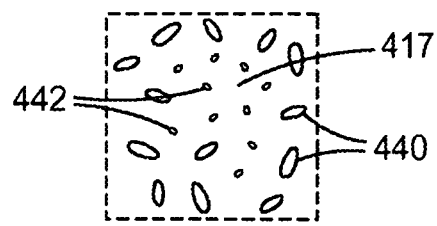

FIG. 4a shows a top view of the culture device of FIG. 3 at a second point in time (e.g., about eight hours after inoculation). FIG. 4b shows an enlargement of a portion of the culture device 410 of FIG. 4a. The enlargement shows a plurality of abiogenic gas bubbles 440, as well as a plurality of diminished abiogenic gas bubbles 442 distributed in the hydrogel 417. The diminished gas bubbles 442 are observably smaller than the typical abiogenic gas bubbles 440 in the growth area. It will be appreciated that the discontinuity of the abiogenic gas bubbles in the culture device 410 can indicate the presence of a microorganism even though there are no other visible indications of a microorganism colony at this point in time.

Figure 5A:
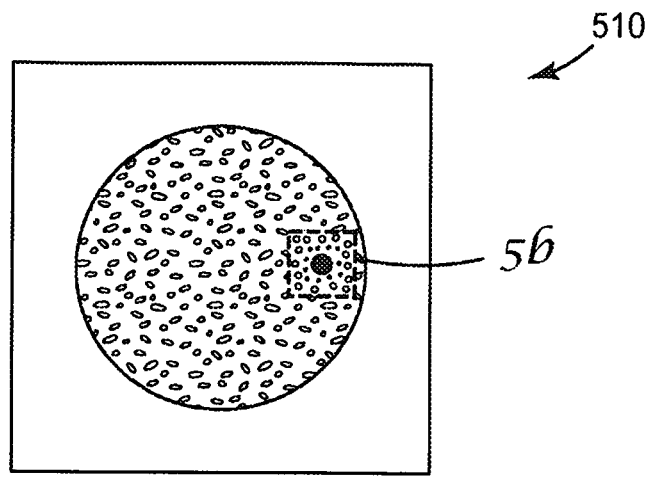
FIG. 5a is a top view of the culture device of FIG. 3 at a third point in time.
Figure 5B:
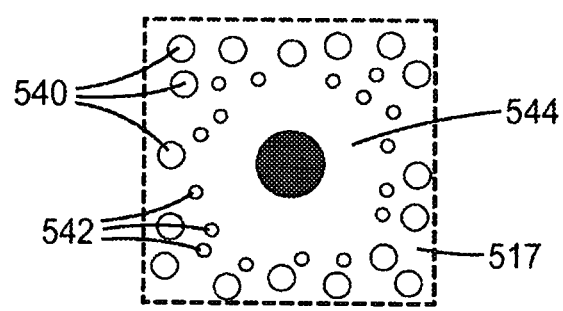

FIG. 5a shows a top view of the culture device of FIG. 3 at a third point in time (e.g., about twelve hours after inoculation). FIG. 5b shows an enlargement of a portion of the culture device 510 of FIG. 5a. The enlargement shows a plurality of abiogenic gas bubbles 540 and a plurality of observably-small abiogenic gas bubbles 542 distributed in the hydrogel 517. FIG. 5b also shows an observably bubble-free zone 544. The abiogenic gas bubbles 540, observably-small abiogenic gas bubbles 542 and bubble-free zone 544 are all proximate a visible microbial colony 560. The observably small abiogenic gas bubbles 542 are distinguishable from the abiogenic gas bubbles 540 in that they are markedly smaller than the normal size range of abiogenic gas bubbles 542 distributed throughout the hydrogel 517.

In some embodiments of the methods, comparing observations of the culture device at two or more time points can confirm the development (e.g., due to the presence of a microorganism) of a discontinuity in the size or presence of abiogenic gas bubbles in the culture device.

In some embodiments of the methods, the culture device is illuminated with ambient light (e.g., sunlight). In some embodiments, the culture device is illuminated with a light source that emits selected wavelengths of light (e.g., white light, ultraviolet light).

In some embodiments, illuminating the culture device comprises illuminating the culture device with a light source positioned facing an outermost first major surface or second major surface of the culture device, as described above. In some embodiments, the observing an indication of growth comprises observing an indication of growth with the observer facing the first major surface or second major surface of the culture device, as described above.

In some embodiments, observing an indication of growth further comprises positioning a contrast layer on the major surface of the culture device opposite the major surface that the observer (e.g., the operator or an imaging device) is facing. In any of the embodiments, detecting the presence or absence of a microorganism can comprise detecting the scattering, absorbance or transmittance of light (e.g., scattering, absorbance, or transmittance of light by a microbial colony). In any of the above embodiments, detecting the presence or absence of a microorganism can comprise enumerating microorganisms.

Detection of an Indication of Microbial Growth Using an Imaging System:

In any of the above embodiments, the method further can comprise providing an imaging system and obtaining an image of the culture device. In these embodiments, detecting the presence or absence of a microorganism comprises displaying, printing, or analyzing the image of the culture device. The imaging system comprises an imaging device and may comprise a processor. In some embodiments, the imaging device can comprise a line-scanner or an area scanner (e.g., a camera). The imaging device can include a monochromatic (e.g., black-and-white) or a polychromatic (e.g., color) scanner. Advantageously, monochromatic imaging systems can provide higher resolution images, which may improve the accuracy of the result and/or reduce the time necessary to detect the presence of microorganisms in the culture device.

In some embodiments, the imaging system further comprises an illumination system. The illumination system may include at least one source of broad-spectrum visible light (e.g., a "white" light). In some embodiments, the illumination system may include at least one source of narrow-spectrum visible light (e.g., a light-emitting diode that emits a relatively narrow bandwidth of visible light such as, for example, red, green, or blue light). In certain embodiments, the illumination system may include a source of narrow-spectrum visible light (e.g., a light-emitting diode) with a light emission peak at about 525 nm.

The image can be obtained from light reflected by the hydrogel in the culture device or the image can be obtained from light transmitted through the hydrogel in the culture device. Suitable imaging systems and corresponding illumination systems are described, for example, in International Patent Publication No. WO 2005/024047 and U.S. Patent Application Publication Nos. US 2004/0101954 and US 2004/0102903, each of which is incorporated herein by reference in its entirety. Non-limiting examples of suitable imaging systems include PETRIFILM Plate Reader (PPR), available from 3M Company (St. Paul, Minn.), the PETRISCAN Colony Counter available from Spiral Biotech (Norwood, Mass.), and PROTOCOL and ACOLYTE plate scanners available from Synbiosis (Cambridge, U.K.)

In some embodiments, obtaining an image comprises obtaining a wavelength-biased image. For example, the imaging system can include a bias filter that biases the light collected by the imaging device. Filter elements are known in the art and include both "cut-off" filters (i.e., filters that allow the passage of light wavelengths either above or below a certain specified wavelength) and "band-pass" filters (i.e., filters that allow the passage of light wavelengths between certain specified upper and lower limits). A bias filter can be positioned between the illumination source and the culture device. Alternatively or additionally, a bias filter can be positioned between the culture device and the imaging device.

In certain preferred embodiments, obtaining an image comprises obtaining an image using a bias filter that selectively allows the passage of red wavelengths. In some embodiments, obtaining an image comprises using a bias filter that selectively allows the passage of wavelengths from about 500 nm to about 550 nm.

Figure 8:
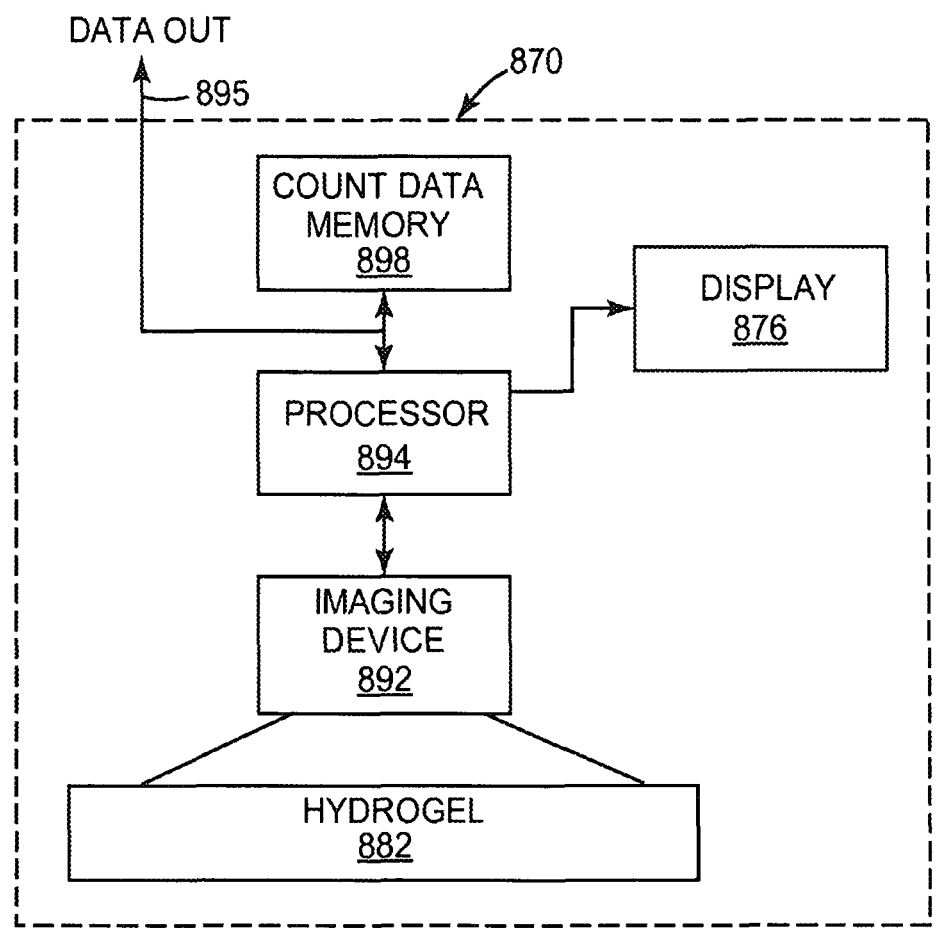
FIG. 8 is a block diagram of one embodiment of a detection system according to the present disclosure.
Figure 9:
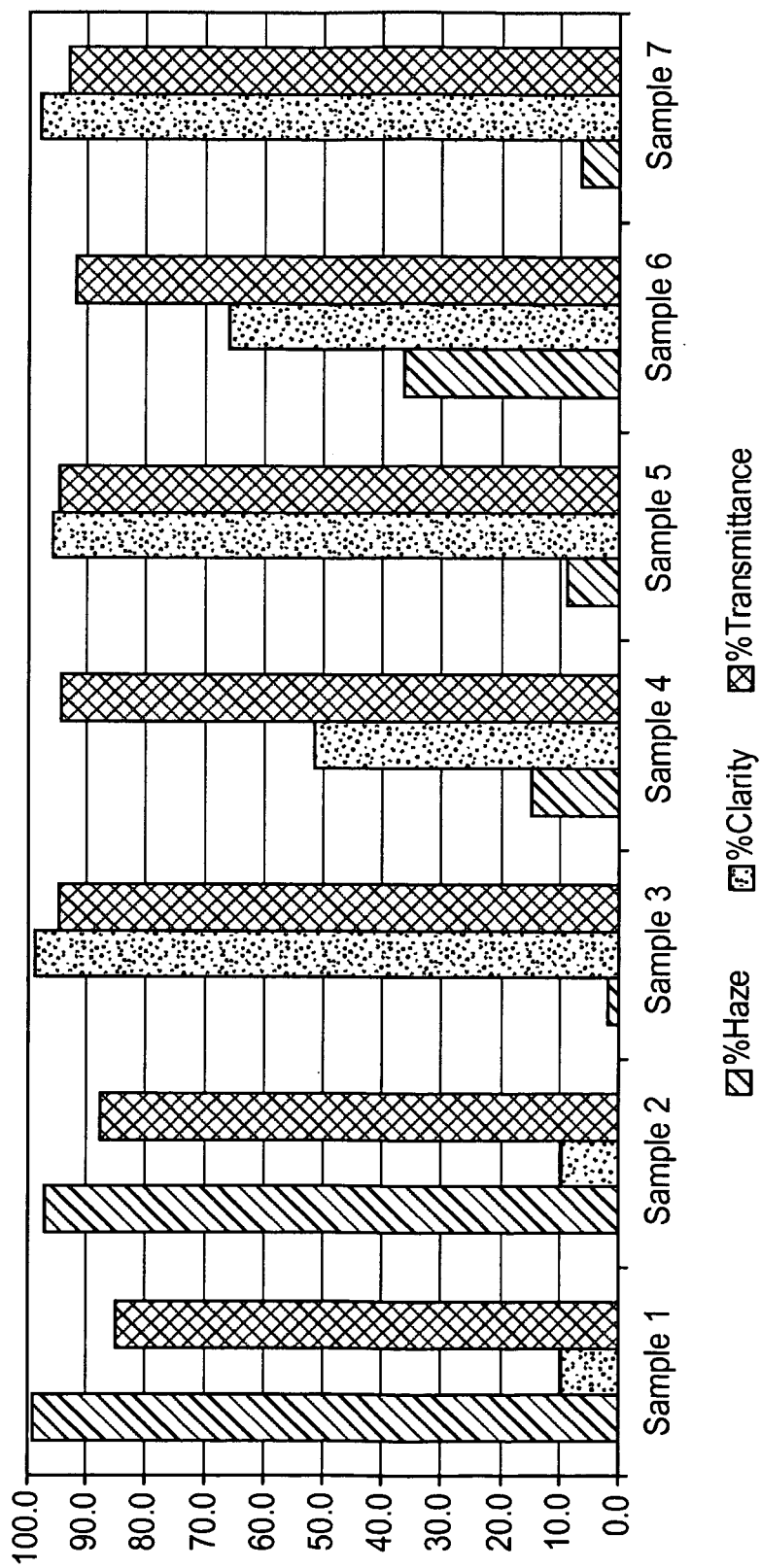
FIG. 9 is a bar graph of optical clarity measurements of thin film culture devices comprising a gelling agent.

FIG. 8 is a block diagram illustrating internal operation of an imaging system 870. As illustrated in FIG. 8, a culture device 882 is positioned in a focal plane (e.g., on a platform, not shown) within imaging system. In accordance with the invention, imaging device 892 may include multi-color illumination systems (not shown) for front and/or back illumination of culture device 882, as well as a monochromatic line or area scanner that captures an image of the culture device 882. In some embodiments, for example, imaging device 892 may take the form of a two-dimensional, monochromatic camera.

In general, imaging device 892 captures images of culture device 882, or at least a portion thereof, during illumination of the culture device with one or more different illumination colors. In some embodiments, multiple images of the same culture device 882 can be generated with various illumination durations or intensities and one or more of the multiple images can be selected for analysis. In some embodiments, selective illumination of a first side and a second side of the culture device 882 can be used to generate multiple images of the culture device and one or more of the images can be selected for analysis. Selection of an image for analysis can be based on, for example, the color contrast and/or object resolution properties of the individual images. Processes for determining the color contrast and object resolution properties of an image are known in the art and are disclosed in, for example, U.S. Pat. No. 6,243,286, which is incorporated herein by reference in its entirety.

A processor 894 controls the operation of imaging device 892. Also shown in FIG. 8 is optional display 876, which can receive an image from the processor 894 for visual review by an operator. In operation, processor 894 controls imaging device 892 to illuminate the culture device 882 and obtain an image. Processor 894 receives image data representing the scanned image from imaging device 892. In some embodiments, processor 894 can select an image, from multiple images, for analysis and/or display. Processor 894 analyzes at least one image of culture device 882 and may produce an analytical result, such as a count of colonies of microorganisms or a determination of the presence or absence of microorganisms in a sample. The analytical result (e.g., a qualitative or quantitative result) can be displayed on display 876, stored in optional data storage memory 898, or retrieved by a host computer (not shown) via optional communication port 895

Analyzing the image of the culture device can comprise using a system to detect color and/or varying shades of a color (e.g., red, green, blue, gray) in an image. Suitable image analysis systems include the image analysis systems described in, for example, U.S. Pat. Nos. 5,448,652; 6,243,486; and 6,153,400; each of which is incorporated herein by reference in its entirety.

In certain embodiments, analyzing the image of the culture device comprises analyzing selected wavelengths of the image. In some embodiments, the image may be a color image collected by illuminating the culture device with a source of broad-spectrum visible light (e.g., a "white" light). In some embodiments, the image may be a color image collected by illuminating the culture device with a plurality of sources of relatively narrow-spectrum visible light (e.g., a combination of light-emitting diodes that each emits a relatively narrow bandwidth of visible light such as, for example, red, green, or blue light). In some embodiments, the image may be a composite image made by combining two or more images collected while illuminating the culture device with two or more different sources of relatively narrow-spectrum visible light (e.g., red, green, or blue light). In some embodiments, the image may be an image collected while illuminating the culture device with a source of relatively narrow-spectrum visible light (e.g., green light). In these embodiments, certain wavelengths of the image can be selected for displaying or printing an image and/or image analysis.

In some embodiments (e.g., wherein the color of the pH indicator ranges from red to yellow), the wavelengths selected for analyzing the image can be wavelengths in the green color range (e.g., wavelengths about 500 nm to about 550 nm). In some embodiments, the wavelengths selected for analysis are wavelengths about 520 nm to about 530 nm. In some embodiments, the wavelength selected for analysis is about 525 nm.

The wavelengths can be selected, for example, by using a computer program that electronically selects a predetermined range of wavelengths in the image for display, printing, and/or analysis. For example, a predetermined green wavelength or range of green wavelengths may be particularly suitable to display, print, or analyze an image of a yellow-colored zone adjacent a colony of microorganisms growing in a red-colored culture medium (e.g., a culture medium comprising chlorophenol red). Any suitable computer program can be used to select a predetermined range of wavelengths in an image. Non-limiting examples of suitable computer programs include PHOTOSHOP CS4 software, available from Adobe Systems, Inc. (San Jose, Calif.) and IMAGE-PRO Plus software, available from Media Cybernetics (Silver Springs, Md.).

In certain embodiments, wherein the image of the culture device has been obtained and/or analyzed in a manner that biases the collection in the image of green wavelengths either transmitted through and/or reflected by the hydrogel in the culture device, the contrast between the pH indicator (e.g., the red-colored chlorophenol red) in the culture medium and the acid zone (e.g., the yellow-colored chlorophenol red) adjacent the bacterial colonies is significantly enhanced. Thus, in these embodiments, lactic acid bacteria are detectable at an earlier time than in comparable methods that do not bias the wavelengths of the image that is collected.

EMBODIMENTS

Embodiment 1 is a method for detecting the presence or absence of a microorganism in a sample, comprising:
providing a liquid sample and a culture device comprising a base member, a cover layer, and a dry cold water-soluble gelling agent disposed on the base member and/or cover layer;
wherein the culture device includes an outermost first major surface, an outermost second major surface, and a growth area;
wherein the culture device is configured to form a highly transmissive optical path extending from the first major surface to the second major surface;
hydrating the growth area of the device with the sample;
incubating the device for a period of time; and
illuminating the growth area with a light source, and
detecting the presence or absence of a microorganism in the growth area;
wherein detecting the presence or absence of a microorganism comprises observing an indication of growth.

Embodiment 2 is the method of embodiment 1, wherein the culture device further comprises an adhesive layer coupled to the base member and/or the cover sheet, wherein the gelling agent is disposed on the adhesive layer.

Embodiment 3 is the method according to embodiment 1 or embodiment 2, wherein illuminating the growth area comprises illuminating the growth area with the light source positioned facing the first major surface of the culture device.

Embodiment 4 is the method according to any one of the preceding embodiments, wherein observing an indication of growth comprises observing the growth area from an observation position facing the first major surface of the culture device.

Embodiment 5 is the method according to embodiment 1 or embodiment 2, wherein illuminating the growth area comprises illuminating the growth area with the light source positioned facing the second major surface of the culture device.

Embodiment 6 is the method according to embodiment 5, wherein observing an indication of growth comprises observing the growth area from a position facing the first major surface of the culture device.

Embodiment 7 is the method of any one of embodiments 1 through 4 wherein, overlapping at least a portion of the growth area of the culture device, the second major surface of the culture device comprises a contrast layer.

Embodiment 8 is the method of embodiment 4, further comprising:
providing a first contrast layer; and
prior to detecting the presence or absence of a microorganism, positioning the first contrast layer proximate the second major surface of the culture device.

Embodiment 9 is the method of embodiment 8, further comprising:
providing a second contrast layer; and
prior to detecting the presence or absence of a microorganism, positioning the second contrast layer proximate the second major surface of the culture device.

Embodiment 10 is the method of any one of embodiments 7 through 9, wherein at least one contrast layer substantially reflects the light.

Embodiment 11 is the method of any one of embodiments 7 through 9, wherein at least one contrast layer is a specularly reflective layer Embodiment 12 is the method of any one of embodiments 7 through 9, wherein at least one contrast layer substantially absorbs selected wavelengths of light.

Embodiment 13 is the method of any one of embodiments 1 through 3, wherein observing an indication of growth comprises observing the growth area from a position facing the second major surface of the culture device.

Embodiment 14 is the method of any one of the preceding embodiments, wherein detecting the presence or absence of a microorganism comprises detecting the scattering, absorbance or transmittance of light.

Embodiment 15 is the method of embodiment 14, wherein detecting the presence or absence of a microorganism comprises detecting the scattering, absorbance or transmittance of light by a colony of microorganisms.

Embodiment 16 is the method of any one of the preceding embodiments, further comprising adding an indicator reagent, and wherein detecting the presence or absence of a microorganism comprises detecting an observable change in the indicator reagent.

Embodiment 17 is the method of any one of the preceding embodiments, wherein detecting the presence or absence of a microorganism comprises detecting a fluorescent signal.

Embodiment 18 is a method for detecting the presence or absence of a microorganism in a sample, comprising:
  providing a sample and a culture device comprising a base member, a cover layer, and a hydrogel comprising a plurality of abiogenic gas bubbles disposed there between;
    wherein the culture device comprises an outermost first major surface and an outermost second major surface;
    wherein the hydrogel defines a growth area;
  inoculating the growth area of the device with the sample at a first point in time;
  incubating the device for a period of time;
  illuminating the growth area with a light source; and
  detecting the presence or absence of a microorganism in the growth area at a second point in time;
    wherein detecting the presence or absence of a microorganism comprises observing an indication of growth;
    wherein observing an indication of growth comprises detecting the diminution or absence of at least one abiogenic gas bubble in the hydrogel at the second point in time.

Embodiment 19 is the method of embodiment 18; wherein providing the culture device comprises providing a thin film culture device that includes a dry, cold water-soluble gelling agent and wherein the method further comprises hydrating the gelling agent with an aqueous liquid.

Embodiment 20 is the method of embodiment 19, wherein the aqueous liquid comprises the sample.

Embodiment 21 is the method of embodiment 19 or embodiment 20, wherein the device is substantially optically transmissible when the gelling agent is hydrated with a clear aqueous liquid.

Embodiment 22 is the method of any one of embodiments 18 through 21, further comprising:
  observing the growth area with regard to the size or absence of the gas bubble at a third point in time, wherein the third point in time occurs after the second point in time; and
  comparing observations of the growth area at two points in time.

Embodiment 23 is the method of any one of embodiments 18 through 22, wherein illuminating the growth area comprises illuminating the growth area with the light source positioned facing the first major surface of the culture device.

Embodiment 24 is the method of any one of embodiments 18 through 23, wherein observing an indication of growth comprises observing the growth area from an observation position facing the first major surface of the culture device.

Embodiment 25 is the method of any one of embodiments 18 through 22, wherein illuminating the growth area comprises illuminating the growth area with the light source positioned facing the second major surface of the culture device.

Embodiment 26 is the method according to embodiment 23, wherein observing an indication of growth comprises observing the growth area from a position facing the first major surface of the culture device.

Embodiment 27 is the method of any one of embodiments 18 through 22 wherein, overlapping at least a portion of the growth area of the culture device, the second major surface of the culture device comprises a contrast layer.

Embodiment 28 is the method of embodiment 22, further comprising:
  providing a first contrast layer; and
  prior detecting the presence or absence of a microorganism, positioning the first contrast layer proximate the second major surface of the culture device.

Embodiment 29 is the method of embodiment 28, further comprising:
  providing a second contrast layer; and
  prior detecting the presence or absence of a microorganism, positioning the second contrast layer proximate the second major surface of the culture device.

Embodiment 30 is the method of any one of embodiments 27 through 29, wherein at least one contrast layer substantially reflects the light.

Embodiment 31 is the method of any one of embodiments 27 through 29, wherein at least one contrast layer is a specularly reflective layer Embodiment 32 is the method of any one of embodiments 27 through 29, wherein at least one contrast layer substantially absorbs selected wavelengths of light.

Embodiment 33 is the method of any one of embodiments 27 through 29, wherein observing an indication of growth comprises observing the growth area from a position facing the second major surface of the culture device.

Embodiment 34 is the method of any one of the preceding embodiments, wherein detecting the presence or absence of a microorganism comprises detecting the scattering, absorbance or transmittance of light.

Embodiment 35 is the method of embodiment 32, wherein detecting the presence or absence of a microorganism comprises detecting the scattering, absorbance or transmittance of light by a colony of microorganisms.

Embodiment 36 is the method of any one of the preceding embodiments, wherein detecting the presence or absence of a microorganism comprises enumerating microorganisms.

Embodiment 37 is the method of any one of the preceding embodiments, wherein detecting the presence or absence of a microorganism comprises detecting and differentiating two or more types of microorganisms.

Embodiment 38 is the method of any one of the preceding embodiments, wherein detecting the presence or absence of a microorganism further comprises:
  providing an imaging system; and
  obtaining an image of the growth area of the culture device;
    wherein observing an indication of growth comprises displaying, printing, or analyzing the image of the growth area.

Embodiment 39 is a device for detecting microorganisms, comprising:
  a base member;
  a cover layer;
  a cold water soluble gelling agent disposed on the adhesive layer
    wherein the device is substantially optically transmissible when the gelling agent is hydrated with a clear aqueous liquid.

Embodiment 40 is the device of embodiment 39, further comprising a first adhesive layer coupled to one of the base member or the cover layer.

Embodiment 41 is the device of embodiment 40, further comprising a second adhesive layer coupled to the other of the base member or cover layer.

Embodiment 42 is the device of embodiment 41, further comprising a nutrient medium disposed on the first or second adhesive layer.

Embodiment 43 is the device of any one of embodiments 40 through 42, further comprising an indicator reagent.

Embodiment 44 is the device of any one of embodiments 40 through 43, further comprising an optical filter layer or a contrast layer.

Embodiment 45 is the device of any one of embodiments 40 through 44, wherein the optical haze of the culture device after hydration of the device with a clear aqueous liquid is ≤95% when measured according to ASTM 1003.

Embodiment 46 is the device of any one of embodiments 40 through 45, wherein the optical clarity of the culture device after hydration of the device with a clear aqueous liquid is ≥10% when measured according to ASTM 1003.

The invention will be further illustrated by reference to the following non-limiting Examples. All parts and percentages are expressed as parts by weight unless otherwise indicated.

EXAMPLES

Example 1

Preparation of a Thin Film Culture Device for Yeast and Mold Detection

A pressure-sensitive adhesive coated polyolefin film having a silicone pressure-sensitive adhesive (3M™ Advanced Polyolefin Diagnostic Tape Catalog #9795R available from 3M Company, St. Paul, Minn.) was used to prepare a powder coated base member for a thin film culture device. The tape had a 2-mil thick clear polyolefin backing and a 2-mil thick layer of silicone pressure-sensitive adhesive, and a white release liner.

A powder nutrient composition was prepared by thoroughly mixing a powder containing 14.3% (all percentages are weight %) pancreatic digest of casein, 25.5% meat peptone, 9.5% yeast extract, 43.4% dextrose, 6% pepticase, 1% ferric ammonium citrate, 0.3% calcium chloride, and sufficient sodium carbonate to adjust the pH to about 7. A gelling powder composition was prepared by mixing in a 1:1 weight ratio xanthan gum powder and locust bean gum powder (both available from Spectrum Chemical Mfg. Corp (Gardena, Calif.)). Sufficient silica (Cab-O-Sil M5 available from Cabot Corp. (Bilerica, Mass.) was added to enhance flow and prevent clumping. The amount is less than about 0.5 weight %. The nutrient composition was mixed with the gelling powder composition in a 1:4 weight ratio. A base member was prepared by sprinkling an excess of the mixed powder composition onto the adhesive coated side of the tape. Excess powder was removed by tilting the sheet and tapping lightly by hand.

A powder gelling composition was prepared by mixing 500 grams of xanthan gum powder (NF Grade Xanthan Gum, obtained from Spectrum Chemical Manufacturing Corp., Gardena, Calif.) and 500 grams of locust bean gum (FCC Grade Locust Bean gum obtained from Spectrum Chemical Manufacturing Corp., Gardena, Calif.) with about 2.9 grams of silica (Cab-O-Sil M5). A cover sheet was prepared by sprinkling the powder composition onto a clear adhesive coated tape (3M™ Advanced Polyolefin Diagnostic Tape Catalog #9795R) and removing the excess powder by tilting the sheet and tapping lightly by hand.

Rectangular plate devices measuring 3 inches by 3.75 inches were cut from the coated sheet to form a base member, and from the coated film to form a cover film. A thin film culture device was assembled by adhering a strip of double coated pressure-sensitive adhesive tape on one end the coated base plate and adhering one end of the cover sheet to it so that the coated surfaces faced each other and the tape functioned as a hinge to hold the cover sheet to the base member FIG. 1.

Example 2

Preparation of a Thin Film Culture Plates for Aerobic Bacteria Detection

A thin film culture device was prepared according to the procedure of Example 1 except that the nutrient composition for the base member was prepared by thoroughly mixing of 22.8 parts of pancreatic digest of casein, 15.9 parts of yeast extract, 45.5 parts of sodium pyruvate, 4.1 parts of dextrose, 9.0 parts of dibasic potassium phosphate, and 2.8 grams of monobasic potassium phosphate. A powder gelling composition was prepared by mixing guar gum (M150 guar MEYPROGAT gum, Meyhall Chemical AG) with a sufficient amount of silica (Cab-O-Sil M5 silica) to prevent clumping and enhance flow (less than about 0.5%)

A cover sheet was prepared according to the procedure of Example 1 except that the powder gelling agent composition was prepared by mixing xanthan gum powder (obtained from Spectrum Chemical Mfg. Corp. (Gardena, Calif.)) locust bean gum powder (obtained from Spectrum Chemical Mfg. Corp. (Gardena, Calif.)) in a 1:1 weight ratio with silica to prevent clumping.

Example 3

Testing of Thin Film Culture Devices for Yeast and Mold

A mold (filamentous fungus), *Paecilomyces* sp. (3M Culture Designation M-10) was propagated by aseptically placing one lyophilized pellet of the mold (obtained from Microbiologics (St. Cloud, Minn.)) in 99 mL Butterfield's Phosphate Diluent (BPD obtained from Edge Biologicals (Memphis, Tenn.)) in a bottle, shaking the bottle, and allowing the mixture to stand at room temperature (about 23° C.) for 30 minutes. The suspension was shaken again, and 2 mL was transferred to a second bottle containing 99 mL of BPD and shaken. One milliliter of the second suspension was inoculated onto a thin film culture device from Example 1 and also onto a control device (3M PETRIFILM Yeast & Mold Count Plate obtained from 3M Company (St. Paul, Minn.)) according to the manufacturer's instructions.

The inoculated devices were incubated simultaneously at 25° C. using an incubation and imaging system as follows. The system included an incubation system having platform coupled to a temperature controller (product number TC-36-25-RS232 obtained from TE Technology, Inc. (Traverse City, Mich.), an illumination source (Leica KL2500LCD 3000 degrees K available from Leica Microsystems GmbH (Wetzlar, Germany), coupled to two illumination guides (Schott A08975 available from Schott North America, Inc. (Southbridge, Mass.), and a camera (NIKON Coolpix 8400. The camera was positioned about 14 inches above the platform to take images at 60 minute intervals during incubation of the thin film culture devices. Two devices, positioned side-by-side on a shiny aluminum plate on the heating platform, were incubated and imaged simultaneously. The two illumination guides were positioned a about a 45 degree angle to the platform and about 8 inches away on opposing sides to direct light at an angle onto the top surface of the devices. Alternatively, instead of an aluminum plate, a mirror or a mirror film such as a Vikuiti™ Enhanced Specular Reflector (available from 3M Company (St. Paul, Minn.)) may be used: A series of fixed temporal (fixed 60 minute automatic acquisition interval) images were taken of the plates during an incubation period of 56 hours. The images were of the device of Example 1 next to a control device, both inoculated with the same culture.

The elapsed time for detection on the device of Example 1 was determined by observing the light scatter through the device and noting the earliest time a change in scatter was detected, as indicated by clearing zones FIGS. 4a and 4b. The elapsed time for the control device was determined by observing the color change of the indicator in the device at the earliest time the change was detected. Observations from the images for *Paecilomyces* sp on the devices of Example 1 and the control are shown in Table 2. The observations note the visual changes of the images at the time elapsed since inoculation. The earliest time at which the visual perception threshold is reached for identifying a colony forming unit (CFU) is noted as well as continuing changes throughout the incubation period. The elapsed time for the earliest detection for all of the plates is summarized in Table 3.

A yeast, *Saccharomyces cerevisiae*, (obtained from Microbiologic (St. Cloud, Minn.) was tested on a device from Example 1 using the same preparation method described above and tested with a control. Results are summarized in Table 3.

TABLE 2

Elapsed time observations of *Paecilomyces* sp

| Time Elapsed | Observations Example 1 | Control |
|---|---|---|
| 32 hours | No observable change; uniform field of small bubbles on plate - FIG. 3 | No observable change |
| 34 hours | Mold is at the CFU visual perception threshold - FIGS. 4a and 4b | No observable change |
| 36 hours | CFU morphology taking form; local bubbles start to diminish in size - FIGS. 5a and 5b | No observable change |
| 56 hours | Mold CFU morphology sharply defined and much larger than the indicator region of the control plate; bubbles reducing in size, then clearing - FIGS. 5 and 5B | CFU at visual perception threshold of blue-green color of indicator. |
| 76 hours* | 1 colony seen on plate; colony larger than indicator regions on control plate | 4 colonies visible |

*The inoculum population was intentionally kept low so the number of colonies was not considered a significant event in this test.

TABLE 3

Earliest elapsed time to detection on yeast and mold plates

| Organism | Elapsed Time Example 1 | Elapsed Time Control | Time difference |
|---|---|---|---|
| *Paecilomyces* sp | 33 hours | 55 hours | 23 hours (42%) |
| *Saccharomyces cerevisiae* | 23 hours | 45 hours | 22 hours (49%) |

Example 4

Testing of Thin Film Culture Devices for Aerobic Bacteria

The control plates used were 3M PETRIFILM Aerobic Count plates, obtained from 3M Company (St. Paul, Minn.).

Two bacterial organisms obtained from the American Type Culture Collection (Manasses, Va.) were used to evaluate the culture device of Example 1 and a control. The organisms were *Escherichia coli* (ATCC 51813) and *Staphylococcus aureus* (ATCC 25923).

Bacterial cultures were prepared by inoculating pure cultures into tryptic soy broth (TSB available from Remel (Lenexa Kans.) and incubated at 35° C. for 21 hours, static. One loop (about 5 microliters) was transferred into fresh TSB and incubated at 35° C. for 21 hours, static. In the primary dilution, 10 microliters of the vortexed culture pipetted into 99 mL of Butterfield's Phosphate Diluent (BPD available from Edge Biologicals (Memphis Tenn.)) in a sample bottle and shaken to mix. In the secondary dilution, 30 microliters from the primary dilution was added to 99 mL of BPD and shaken to mix. One milliliter of the secondary dilution, containing about 10 colony forming units (CFUs), was used to inoculate a 3M PETRIFILM Aerobic Count plate according to the manufacturer's instructions. One milliliter was used to inoculate devices of Example 1 in the same manner. Inoculated plates were incubated at 35° C. for 48 hours and imaged using the system and method described in Example 3. Images were taken at 30 minute intervals. The elapsed time for observing the first CFUs is summarized in Table 4.

TABLE 4

Elapsed time observation of aerobic bacteria plates

| Organism | Elapsed Time Example 1 | Elapsed Time Control | Time difference |
|---|---|---|---|
| *Escherichia coli* | 7.5 hours | 16.5 hours | 9 hours (55%) |
| *Staphylococcus aureus* | 8 hours | 12.5 hours | 4.5 hours (36%) |

Example 5

Use of a Contrast Layer to Enhance Detection

A culture device was prepared according to the method of Example 2 and tested according to the method of Example 4 using *Escherichia coli* (ATCC 51813). A control device was also prepared and tested. The culture devices were incubated at 35° C. for 48 hours. The device of Example 2 with *E. coli* was placed on a reflector (Vikuiti™ Enhanced Specular Reflector. The colonies were noticeable more apparent to the naked eye when the device was observed on the reflector. The reflector background made the CFU morphology easier to see because of the enhanced contrast. There was also better contrast between the bubble and bubble-free zones. A white paper printed with yellow gridlines, used in the control, was placed between the reflector and the bottom surface of the culture device. The changes in morphology and bubble clearing were less visible with the paper.

The cover film of the control was carefully lifted and a piece of the Vikuiti™ Enhanced Specular Reflector was inserted so that it covered about ⅓ of the inoculated zone. Red colonies from the indicator were quite visible on the bubbles with the reflector inserted. The reflector enhanced the visibility of the bubble clearing zones.

Example 6

Thin Film Culture Device with Modified Guar Gum

A thin film culture device was prepared according to the method of Example 2 except that the gum used was a modified guar powder (Jaguar C162 obtained from Rhodia).

Example 7

Haze, Clarity, and Transmittance Properties of Films and Culture Devices

Thin film culture devices and constituent parts were measured for optical properties—light transmittance, haze, and clarity. The % haze is an indication of the amount of light scattering and is an indication of how easy it is to observe changes in the CFU morphology during incubation. Measurements for haze, clarity and transmittance were measured in the transmission mode according to the manufacturer's instructions and in conformance to ASTM 1003 using a light measuring instrument (BYK Gardner Haze-gard plus, Catalog #4725, Serial #102485 available from BYK-Gardner USA (Columbia, Md.). A baseline for the instrument was established without a device under test, i.e., the tape or the thin film culture device, etc. in the sample path and results were 0% haze, 100% clarity, and 100% transmission as expected.

Optical properties are shown in Table 9. Each point on the graph represents an average of 4 or 5 readings. Sample 1 was a dry powder coated cover sheet from a 3M PETRIFILM Aerobic Count plate (AC plate) tested with the powder side facing the light detector sphere. Sample 2 was two cover sheets from AC plates inoculated with a buffer. Sample 3 was a biaxially oriented polypropylene (BOPP) film without adhesive from an AC plate. Sample 4 was the BOPP film with the adhesive from an AC Plate. Sample 5 was 3M™ Advanced Polyolefin Diagnostic Tape Catalog #9795R. Sample 6 was the base member coupled with the cover sheet from Example 2 and inoculated with liquid diluent. Sample 7 was the device of Example 6 inoculated with a liquid diluent.

Sample 5, without the liner had an average light transmittance of 94.5%, haze of 8.8%, and clarity of 95.8%. Sample 6, the thin film culture device after inoculation had a light transmittance of 91.9%, haze of 34.7%, and clarity of 66%.

Example 8

Sterilization of Ingredients

The powders for the cover sheets of Examples 1 and 2 are sterilized by treatment with ethylene oxide gas and then aerated to remove any residual ethylene oxide gas prior to coating.

Example 9

Sterilization of Thin Film Culture Devices

Thin film culture devices of Examples 1 and 2 are placed in an ethylene oxide atmosphere in an enclosed chamber and sterilized.

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

The invention claimed is:

1. A method for detecting the presence or absence of an aerobic or a facultatively anaerobic microorganism in a sample, comprising:
    providing a sample and a culture device comprising a base member, a cover layer, and a hydrogel comprising a plurality of abiogenic gas bubbles disposed there between;
        wherein the culture device comprises an outermost first major surface and an outermost second major surface;
        wherein the hydrogel defines a growth area;
        wherein providing the culture device comprises providing a thin film culture device that includes a dry, cold water-soluble gelling agent and wherein the method further comprises hydrating the gelling agent with an aqueous liquid;
    inoculating the growth area of the device with the sample at a first point in time;
    incubating the device for a period of time;
    illuminating the growth area with a light source;
    observing an abiogenic gas bubble in the hydrogel in the growth area at a second point in time;
    observing the growth area with regard to the size or absence of the abiogenic gas bubble at a third point in time, wherein the third point in time occurs after the second point in time;
    comparing observations of the growth area at two points in time; and
    detecting the presence or absence of an aerobic or a facultatively anaerobic microorganism in the growth area at a third point in time;
    wherein detecting the presence or absence of an aerobic or a facultatively anaerobic microorganism comprises observing an indication of growth;
    wherein observing an indication of growth comprises detecting a diminution or absence of the abiogenic gas bubble in the hydrogel at the third point in time;
    wherein detecting the diminution or absence of the abiogenic gas bubble in the hydrogel at the third point in time indicates the presence of an aerobic or a facultatively anaerobic microorganism in the sample.

2. The method of claim 1, wherein illuminating the growth area comprises illuminating the growth area with the light source positioned facing the first major surface of the culture device.

3. The method according to claim 2, wherein observing an indication of growth comprises observing the growth area from a position facing the first major surface of the culture device.

4. The method of claim 1, wherein observing an indication of growth comprises observing the growth area from an observation position facing the first major surface of the culture device.

5. The method of claim 1, wherein illuminating the growth area comprises illuminating the growth area with the light source positioned facing the second major surface of the culture device.

6. The method of claim 1, overlapping at least a portion of the growth area of the culture device, the second major surface of the culture device comprises a contrast layer.

7. The method of claim 6, wherein observing an indication of growth comprises observing the growth area from a position facing the second major surface of the culture device.

8. The method of claim 1, wherein detecting the presence or absence of a microorganism comprises detecting and differentiating two or more types of microorganisms.

9. The method of claim 1, wherein detecting the presence or absence of a microorganism further comprises:
    providing an imaging system; and
    obtaining an image of the growth area of the culture device;
    wherein observing an indication of growth comprises displaying, printing, or analyzing the image of the growth area.

* * * * *